United States Patent [19]

Winter et al.

[11] Patent Number: 5,672,668

[45] Date of Patent: *Sep. 30, 1997

[54] PROCESS FOR THE PREPARATION OF POLYOLEFINS

[75] Inventors: Andreas Winter, Glashütten/Ts; Martin Antberg, Hofheim/Ts; Bernd Bachmann, Eppstein/Ts; Volker Dolle, Bensheim; Frank Küber, Oberursel; Jürgen Rohrmann, Kelkheim/Ts; Walter Spaleck, Liederbach, all of Germany

[73] Assignee: Hoechst Aktiengesellschaft, Frankfurt, Germany

[*] Notice: The term of this patent shall not extend beyond the expiration date of Pat. No. 5,304,416.

[21] Appl. No.: 107,187

[22] Filed: Aug. 16, 1993

[30] Foreign Application Priority Data

Aug. 15, 1992 [DE] Germany .......................... 42 27 049.9

[51] Int. Cl.$^6$ .................................................. C08F 4/642
[52] U.S. Cl. ........................ 526/127; 526/126; 526/132; 526/133; 526/134; 526/150; 526/151; 526/160; 526/170; 526/351; 526/943
[58] Field of Search ........................ 526/160, 121, 526/122, 127, 132, 150, 151, 126, 133, 134, 170, 943

[56] References Cited

U.S. PATENT DOCUMENTS

| 5,145,819 | 9/1992 | Winter et al. | 502/117 |
|---|---|---|---|
| 5,278,264 | 1/1994 | Spaleck et al. | 526/127 |
| 5,304,614 | 4/1994 | Winter et al. | 526/127 |
| 5,328,969 | 7/1994 | Winter et al. | 526/127 |

FOREIGN PATENT DOCUMENTS

| 0503422 | 9/1992 | European Pat. Off. |
|---|---|---|
| 0 530 647 | 3/1993 | European Pat. Off. |
| 3826075 | 2/1990 | Germany . |

OTHER PUBLICATIONS

Stevens, "Metallocene and Other Single Site Catalysts," The Dow Chemical Co., PTO Presentation, Dec. 8, 1994.
High Molecular Weight Polypropylene through Specifically Designed Zirconocene Catalysts by Walter Spaleck et al., *Angewandte Chemie*, Bd. 31, Nr. 10, Oct. 1992, pp. 1347–1350, Weinheim, Germany.
ansa–Metallocene derivatives by Peter Burger et al., *Journal of Organometallic Chemistry*, Bd. 417, Nr. 1–2, Oct. 1, 1991, p. 9–27, Lausanne.
Mechanisms of Stereochemical Control in Propylene Polymerizations with Soluble Group 4B Metallocene/Methylalumoxane Catalysts by John A. Ewen, *J. Am. Chem. Soc.*, Bd. 106, 1984, p. 6355–6364.

*Primary Examiner*—Romulo H. Delmendo
*Attorney, Agent, or Firm*—John M. Genova

[57] ABSTRACT

A process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from –60° to 200° C., at a pressure of from 0.5 to 100 bar, in solution, in suspension or in the gas phase, in the presence of a catalyst formed from a metallocene in the meso-form or a meso:rac mixture, with meso:rac>1:99, as transition-metal compound and a cocatalyst, wherein the metallocene is a compound of the formula I,

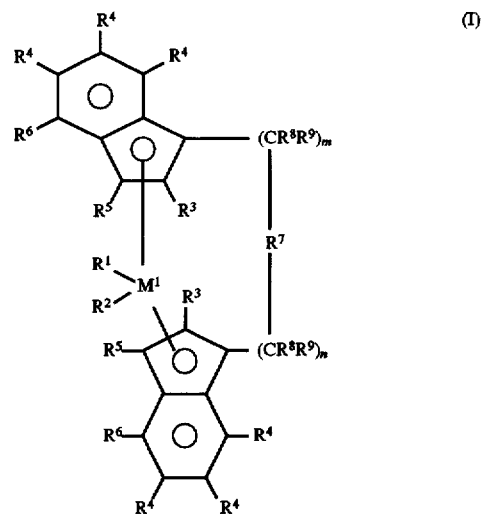

in which $M^1$ is Zr or Hf, $R^1$ and $R^2$ are identical or different and are methyl or chlorine, $R^3$ and $R^6$ are identical or different and are methyl, isopropyl, phenyl, ethyl or trifluoromethyl, $R^4$ and $R^5$ are hydrogen or as defined for $R^3$ and $R^6$, or $R^4$ forms an aliphatic or aromatic ring with $R^6$, or adjacent radicals $R^4$ form a ring of this type, and $R^7$ is a

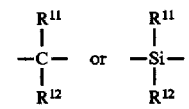

radical, and m plus n is zero or 1.

10 Claims, No Drawings

PROCESS FOR THE PREPARATION OF POLYOLEFINS

DESCRIPTION

For the preparation of highly isotactic polyolefins by means of stereospecific racemic metallocene/cocatalyst systems, the highest possible isotacticity is desired. This means that very stereoselective racemic metallocene types are employed which are able to build up polymer chains having very few construction faults. The consequence of this is that products having high crystallinity, high melting point and thus also high hardness and excellent modulus of elasticity in flexing are obtained as desired.

However, it is disadvantageous that these polymers are difficult to process, and in particular problems occur during extrusion, injection molding and thermoforming. Admixing of flow improvers and other modifying components could help here, but results in the good product properties, such as, for example, the high hardness, being drastically reduced. In addition, tackiness and fogging also occur. The object was thus to improve the processing properties of highly isotactic polyolefins of this type without in this way impairing the good properties of the moldings produced therefrom.

Surprisingly, we have found that if rac/meso mixtures of certain metallocenes are used, the processing problems can be eliminated without the abovementioned good product properties being lost.

In addition, the use of these specific metallocenes in their pure meso-form makes it possible to prepare high-molecular-weight atactic polyolefins which can be homogeneously admixed, as additives, with other polyolefins.

This was not possible with the low-molecular weight polyolefins accessible hitherto due to the large differences in viscosity between the polyolefin matrix and the atactic component.

Such admixtures improve polyolefin moldings with respect to their surface gloss, their impact strength and their transparency. In addition, the processing properties of such polyolefins are likewise improved by admixing the high-molecular-weight atactic polyolefin. Likewise, tackiness and fogging do not occur.

Homogeneous miscibility of the atactic component is so important because only with a homogeneous material can a usable molding with a good surface and long service life be produced and only in the case of homogeneous distribution do the qualities of the atactic component come out in full.

The invention thus relates to the preparation of polyolefins which 1) are atactic, i.e. have an isotactic index of ≦60%, and are high-molecular, i.e. have a viscosity index of >80 cm$^3$/g and a molecular weight $M_w$ of >100,000 g/mol with a polydispersity $M_w/M_n$ of ≦4.0, or
2) comprise at least two types of polyolefin chains, namely
   a) a maximum of 99% by weight, preferably a maximum of 98% by weight, of the polymer chains in the polyolefin as a whole comprise α-olefin units linked in a highly isotactic manner, with an isotactic index of >90% and a polydispersity of ≦4.0, and
   b) at least 1% by weight, preferably at least 2% by weight, of the polymer chains in the polyolefin as a whole comprise atactic polyolefins of the type described under 1).

Polyolefins which conform to the description under 2) can either be prepared directly in the polymerization or are prepared by melt-mixing in an extruder or compounder.

The invention thus relates to a process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from −60° to 200° C., at a pressure of from 0.5 to 100 bar, in solution, in suspension or in the gas phase, in the presence of a catalyst formed from a metallocene as transition-metal compound and a cocatalyst, wherein the metallocene is a compound of the formula I which is used in the pure meso-form for the preparation of polyolefins of type 1 and used in a meso:rac ratio of greater than 1:99, preferably greater than 2:98, for the preparation of type 2 polyolefins,

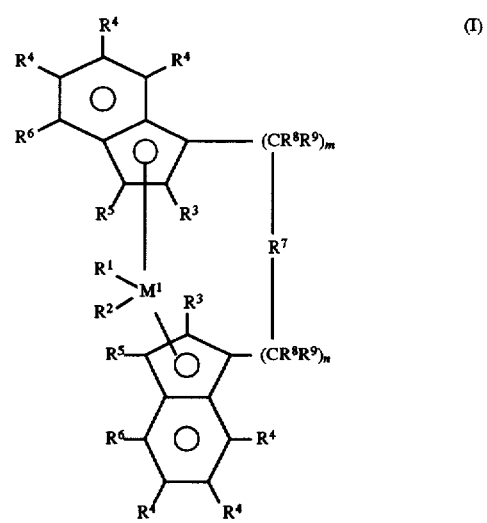

in which $M^1$ is a metal from group IVb, Vb or rib of the Periodic Table, $R^1$ and $R^2$ are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group, or a halogen atom, the radicals $R^4$ and $R^5$ are identical or different and are a hydrogen atom, a halogen atom, a $C_1$-$C_{10}$-alkyl group, which may be halogenated, a $C_6$-$C_{10}$-aryl group, which may be halogenated, and an —NR$^{10}_2$, —SR$^{10}$, —OSiR$^{10}_3$, —SiR$^{10}_3$ or —PR$^{10}_2$ radical in which R$^{10}$ is a halogen atom, a $C_1$-$C_{10}$-alkyl group or a $C_6$-$C_{10}$-aryl group, $R^3$ and $R^6$ are identical or different and are as defined as for $R^4$, with the proviso that $R^3$ and $R^6$ are not hydrogen, or two or more of the radicals $R^3$ to $R^6$, together with the atoms connecting them, form a ring system, $R^7$

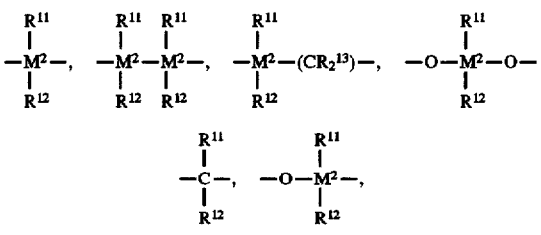

=BR$^{11}$, =AlR$^{11}$, —Ge—, —Sn—, —O—, —S—, =SO, =SO$_2$, =NR$^{11}$, =CO, =PR$^{11}$ or =P(O)R$^{11}$, where $R^{11}$, $R^{12}$ and $R^{13}$ are identical or different and are a hydrogen atom, a halogen atom, a $C_1$-$C_{10}$-alkyl group, a $C_1$-$C_{10}$-fluoroalkyl group, a $C_6$-$C_{10}$-aryl group, a $C_6$-$C_{10}$-fluoroaryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or $R^{11}$ and $R^{12}$ or $R^{11}$ and $R^{13}$, in each case together with the atoms connecting them, form a ring, $M^2$ is silicon, germanium or tin, $R^8$ and $R^9$ are identical or different and are as defined for $R^{11}$, and m and n are identical or different and are zero, 1 or 2, where m plus n is zero, 1 or 2.

Alkyl is straight-chain or branched alkyl. Halogen (halogenated) means fluorine, chlorine, bromine or iodine, preferably fluorine or chlorine.

The substitutents $R^3$, $R^4$, $R^5$ and $R^6$ may be different in spite of the same indexing.

The catalyst to be used for the process according to the invention comprises a cocatalyst and a metallocene of the formula I.

In the formula I, $M^1$ is a metal from group IVb, Vb or VIb of the Periodic Table, for example titanium, zirconium, hafnium, vanadium, niobium, tantalum, chromium, molybdenum or tungsten, preferably zirconium, hafnium or titanium.

$R^1$ and $R^2$ are identical or different and are a hydrogen atom, a $C_1$-$C_{10}$-, preferably $C_1$-$C_3$-alkyl group, a $C_1$-$C_{10}$-, preferably $C_1$-$C_3$-alkoxy group, a $C_6$-$C_{10}$-, preferably $C_6$-$C_8$-aryl group, a $C_6$-$C_{10}$-, preferably $C_6$-$C_8$-aryloxy group, a $C_2$-$C_{10}$-, preferably $C_2$-$C_4$-alkenyl group, a $C_7$-$C_{40}$-, preferably $C_7$-$C_{10}$-arylalkyl group, a $C_7$-$C_{40}$-, preferably a $C_7$-$C_{12}$-alkylaryl group, a $C_8$-$C_{40}$-, preferably a $C_8$-$C_{12}$-arylalkenyl group, or a halogen atom, preferably chlorine.

The radicals $R^4$ and $R^5$ are identical or different and are a hydrogen atom, a halogen atom, preferably a fluorine, chlorine or bromine atom, a $C_1$-$C_{10}$-, preferably $C_1$-$C_4$-alkyl group, which may be halogenated, a $C_6$-$C_{10}$-, preferably a $C_6$-$C_9$-aryl group, which may be halogenated, an $-NR^{10}{}_2$, $-SR^{10}$, $-OSiR^{10}{}_3$, $-SiR^{10}{}_3$ or $-PR^{10}{}_2$ radical, in which $R^{10}$ is a halogen atom, preferably a chlorine atom, or a $C_1$-$C_{10}$-, preferably a $C_1$-$C_3$-alkyl group, or a $C_6$-$C_{10}$-, preferably $C_6$-$C_8$-aryl group. $R^4$ and $R^5$ are particularly preferably hydrogen, $C_1$-$C_4$-alkyl or $C_6$-$C_9$-aryl.

$R^3$ and $R^6$ are identical or different and are defined for $R^4$, with the proviso that $R^3$ and $R^6$ must not be hydrogen. $R^3$ and $R^6$ are preferably ($C_1$-$C_4$)-alkyl or $C_6$-$C_9$-aryl, both of which may be halogenated, such as methyl, ethyl, propyl, isopropyl, butyl, isobutyl, trifluoromethyl, phenyl, tolyl or mesityl, in particular methyl, isopropyl or phenyl.

Two or more of the radicals $R^3$ to $R^6$ may alternatively, together with the atoms connecting them, form an aromatic or aliphatic ring system. Adjacent radicals, in particular $R^4$ and $R^6$, together preferably form a ring.

$R^7$

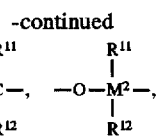

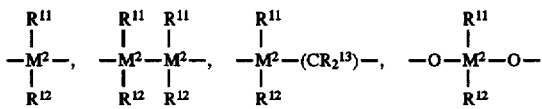

$=BR^{11}$, $=AlR^{11}$, $-Ge-$, $-Sn-$, $-O-$, $-S-$, $=SO$, $=SO_2$, $=NR^{11}$, $=CO$, $=PR^{11}$ or $=P(O)R^{11}$, where $R^{11}$, $R^{12}$ and $R^{13}$ are identical or different and are a hydrogen atom, a halogen atom, a $C_1$-$C_{10}$-, preferably $C_1$-$C_4$-alkyl group, in particular a methyl group, a $C_1$-$C_{10}$-fluoroalkyl group, preferably a $CF_3$ group, a $C_6$-$C_{10}$-, preferably $C_6$-$C_8$-aryl group, a $C_6$-$C_{10}$-fluoroaryl group, preferably a pentafluorophenyl group, a $C_1$-$C_{10}$-, preferably a $C_1$-$C_4$-alkoxy group, in particular a methoxy group, a $C_2$-$C_{10}$-, preferably $C_2$-$C_4$-alkenyl group, a $C_7$-$C_{40}$-, preferably $C_7$-$C_{10}$-arylalkyl group, a $C_8$-$C_{40}$-, preferably $C_8$-$C_{12}$-arylalkenyl group or a $C_7$-$C_{10}$-, preferably $C_7$-$C_{12}$-alkylaryl group, or $R^{11}$ and $R^{12}$ or $R^{11}$ and $R^{13}$, in each case together with the atoms connecting them, form a ring.

$M^2$ is silicon, germanium or tin, preferably silicon or germanium.

$R^7$ is preferably $=CR^{11}R^{12}$, $=SiR^{11}R^{12}$, $=GeR^{11}R^{12}$, $-O-$, $-S-$, $=SO$, $=PR^{11}$ or $=P(O)R^{11}$.

$R^8$ and $R^9$ are identical or different and are as defined for $R^{11}$.

m and n are identical or different and are zero, 1 or 2, preferably zero or 1, where m plus n is zero, 1 or 2, preferably zero or 1.

Particularly preferred metallocenes are thus the compounds of the formulae A and B

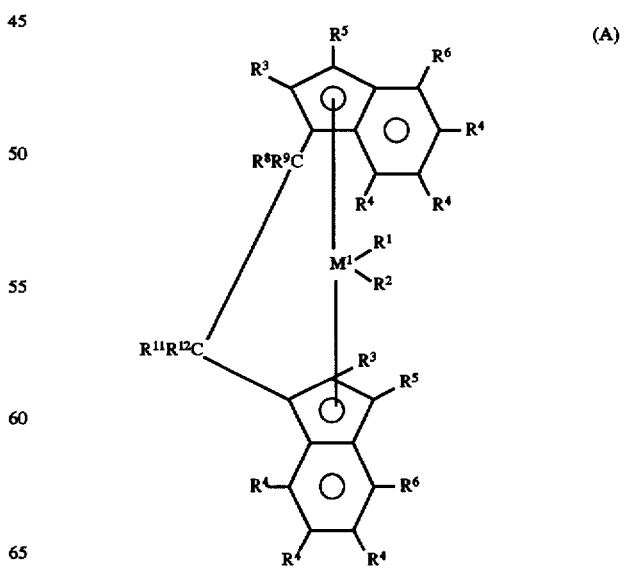

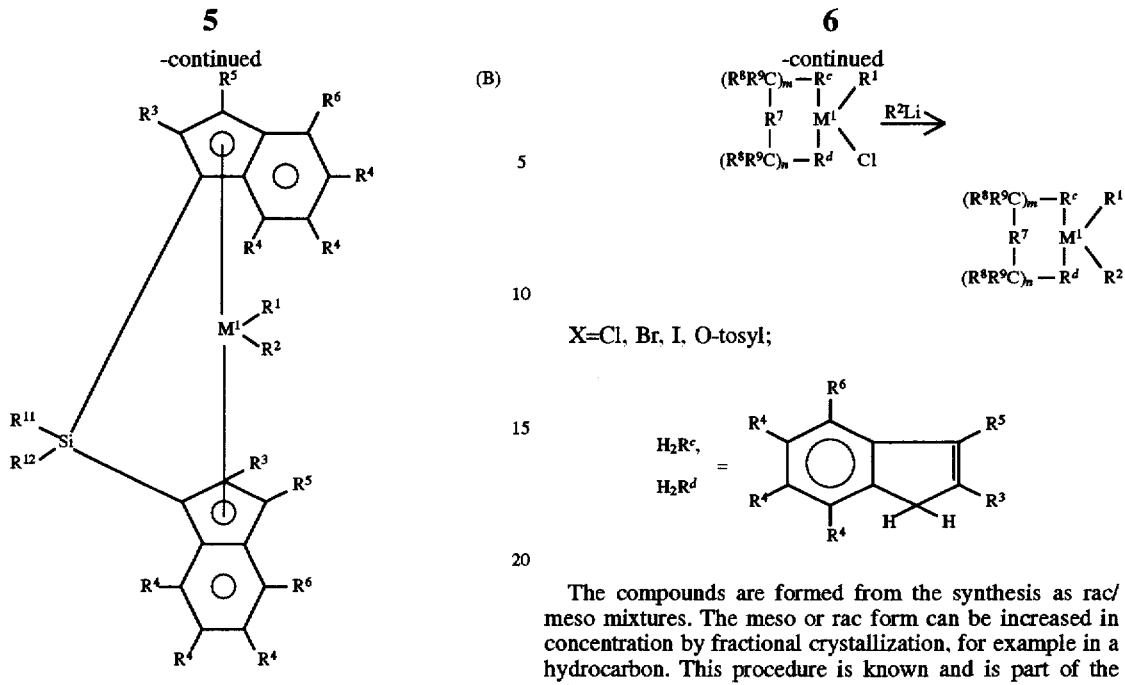

where $M^1$ is Zr or Hf; $R^1$ and $R^2$ are methyl or chlorine; $R^3$ and $R^6$ are methyl, isopropyl, phenyl, ethyl or trifluoromethyl; $R^4$ and $R^5$ are hydrogen or as defined for $R^3$ and $R^6$, or $R^4$ can form an aliphatic or aromatic ring with $R^6$; the same also applies to adjacent radicals $R^4$; and $R^8$, $R^9$, $R^{11}$ and $R^{12}$ are as defined above, in particular the compounds I listed in the working examples.

This means that the indenyl radicals of the compounds I are substituted, in particular, in the 2,4-position, in the 2,4,6-position, in the 2,4,5-position or in the 2,4,5,6-position, and the radicals in the 3- and 7-positions are preferably hydrogen.

Nomenclature:

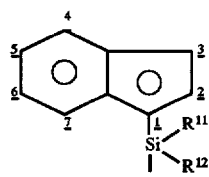

The metallocenes described above can be prepared by the following reaction scheme, which is known from the literature:

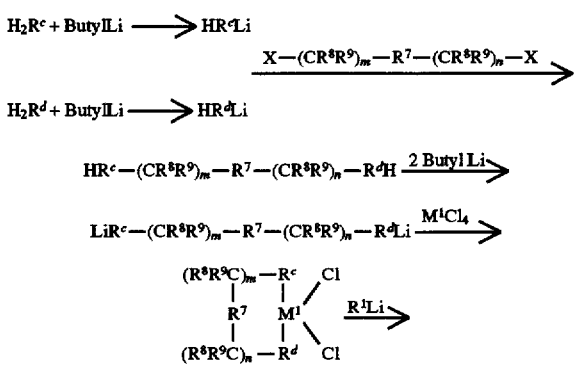

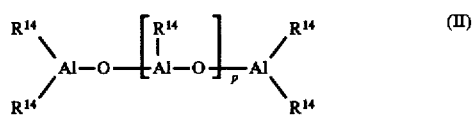

X=Cl, Br, I, O-tosyl;

$H_2R^c$,
$H_2R^d$ =

(indene structure with $R^3$, $R^4$, $R^5$, $R^6$ substituents)

The compounds are formed from the synthesis as rac/meso mixtures. The meso or rac form can be increased in concentration by fractional crystallization, for example in a hydrocarbon. This procedure is known and is part of the prior art.

The cocatalyst used according to the invention is preferably an aluminoxane of the formula (II)

$$R^{14}\!\!\diagdown_{\!\!\!Al-O-\!\!\left[\!\!\begin{array}{c}R^{14}\\|\\Al-O\end{array}\!\!\right]_p\!\!-Al\diagup^{R^{14}}_{\!\!\diagdown R^{14}}}^{R^{14}} \quad (II)$$

for the linear type and/or of the formula (III)

$$-\!\!\left[\!\!\begin{array}{c}R^{14}\\|\\O-Al\end{array}\!\!\right]_{p+2}\!\!- \quad (III)$$

for the cyclic type, where, in the formulae (II) and (III), the radicals $R^{14}$ may be identical or different and are a $C_1$-$C_6$-alkyl group, a $C_6$-$C_{18}$-aryl group, benzyl or hydrogen, and p is an integer from 2 to 50, preferably from 10 to 35.

The radicals $R^{14}$ are preferably identical and are preferably methyl, isobutyl, phenyl or benzyl, particularly preferably methyl.

If the radicals $R^{14}$ are different, they are preferably methyl and hydrogen or alternatively methyl and isobutyl, where hydrogen and isobutyl are preferably present to the extent of 0.01–40% (number of radicals $R^{14}$).

The aluminoxane can be prepared in various ways by known processes. One of the methods is, for example, to react an aluminum hydrocarbon compound and/or a hydridoaluminum hydrocarbon compound with water (in gas, solid, liquid or bonded form—for example as water of crystallization) in an inert solvent (such as, for example, toluene). In order to prepare an aluminoxane containing different alkyl groups $R^{14}$ two different trialkylaluminum compounds ($AlR_3+AlR'_3$) corresponding to the desired composition are reacted with water (cf. S. Pasynkiewicz, Polyhedron 9 (1990) 429 and EP-A 302 424).

The precise structure of the aluminoxanes II and III is unknown.

Regardless of the preparation method, all the aluminoxane solutions have in common a varying content of unreacted aluminum starting compound, in free form or as an adduct.

It is possible to preactivate the metallocene by means of an aluminoxane of the formula (II) and/or (III) before use in the polymerization reaction. This significantly increases the polymerization activity and improves the grain morphology.

The preactivation of the transition-metal compound is carried out in solution. The metallocene is preferably dissolved in a solution of the aluminoxane in an inert hydrocarbon. Suitable inert hydrocarbons are aliphatic and aromatic hydrocarbons. Toluene is preferably used.

The concentration of the aluminoxane in the solution is in the range from about 1% by weight to the saturation limit, preferably from 5 to 30% by weight, in each case based on the solution as a whole. The metallocene can be employed in the same concentration, but is preferably employed in an amount of from $10^{-4}$ to 1 mol per mol of aluminoxane. The preactivation time is from 5 minutes to 60 hours, preferably from 5 to 60 minutes. The reaction is carried out at a temperature of from $-78°$ C. to $100°$ C., preferably from $0°$ to $70°$ C.

The metallocene can also be prepolymerized or applied to a support. Prepolymerization is preferably carried out using the (or one of the) olefin(s) employed in the polymerization.

Examples of suitable supports are silica gels, aluminum oxides, solid aluminoxane or other inorganic support materials. Another suitable support material is a polyolefin powder in finely divided form.

According to the invention, compounds of the formulae $R_xNH_{4-x}BR'_4$, $R_xPH_{4-x}BR'_4$, $R_3CBR'_4$ or $BR'_3$ can be used as suitable cocatalysts instead of or in addition to an aluminoxane. In these formulae, x is a number from 1 to 4, preferably 3, the radicals R are identical or different, preferably identical, and are $C_1$-$C_{10}$-alkyl, or $C_6$-$C_{18}$-aryl or 2 radicals R, together with the atom connecting them, form a ring, and the radicals R' are identical or different, preferably identical, and are $C_6$-$C_{18}$-aryl, which may be substituted by alkyl, haloalkyl or fluorine.

In particular, R is ethyl, propyl, butyl or phenyl, and R' is phenyl, pentafluorophenyl, 3,5-bistrifluoromethylphenyl, mesityl, xylyl or tolyl (cf. EP-A 277 003, EP-A 277 004 and EP-A 426 638).

When the abovementioned cocatalysts are used, the actual (active) polymerization catalyst comprises the product of the reaction of the metallocene and one of said compounds. For this reason, this reaction product is preferably prepared first outside the polymerization reactor in a separate step using a suitable solvent.

In principle, suitable cocatalysts are according to the invention any compounds which, due to their Lewis acidity, are able to convert the neutral metallocene into a cation and stabilize the latter ("labile coordination"). In addition, the cocatalyst or the anion formed therefrom should not undergo any further reactions with the metallocene cation formed (cf. EP-A 427 697).

In order to remove catalyst poisons present in the olefin, purification by means of an alkylaluminum compound, for example $AlMe_3$ or $AlEt_3$, is advantageous. This purification can be carried out either in the polymerization system itself, or the olefin is brought into contact with the Al compound before addition to the polymerization system and is subsequently separated off again.

The polymerization or copolymerization is carried out in known manner in solution, in suspension or in the gas phase, continuously or batchwise, in one or more steps, at a temperature of from $-60°$ to $200°$ C., preferably from $30°$ to $80°$ C., particularly preferably at from $50°$ to $80°$ C. The polymerization or copolymerization is carried out using olefins of the formula $R^a$—CH=CH—$R^b$. In this formula, $R^a$ and $R^b$ are identical or different and are a hydrogen atom or an alkyl radical having 1 to 14 carbon atoms. However, $R^a$ and $R^b$, together with the carbon atoms connecting them, may alternatively form a ring. Examples of such olefins are ethylene, propylene, 1-butene, 1-hexene, 4-methyl-1-pentene, 1-octene, norbornene and norbornadiene. In particular, propylene and ethylene are polymerized.

If necessary, hydrogen is added as molecular weight regulator and/or to increase the activity. The overall pressure in the polymerization system is 0.5 to 100 bar. The polymerization is preferably carried out in the industrially particularly relevant pressure range of from 5 to 64 bar.

The metallocene is used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. The other cocatalysts mentioned are used in approximately equimolar amounts with respect to the metallocene. In principle, however, higher concentrations are also possible.

If the polymerization is carried out as a suspension or solution polymerization, an inert solvent which is customary for the Ziegler low-pressure process is used. For example, the process is carried out in an aliphatic or cycloaliphatic hydrocarbon; examples of such hydrocarbons which may be mentioned are propane, butane, pentane, hexane, heptane, isooctane, cyclohexane and methylcyclohexane.

It is also possible to use a benzine or hydrogenated diesel oil fraction. Toluene can also be used. The polymerization is preferably carried out in the liquid monomer.

If inert solvents are used, the monomers are metered in as gases or liquids.

The polymerization can have any desired duration, since the catalyst system to be used according to the invention only exhibits a slight drop in polymerization activity as a function of time.

The process according to the invention is distinguished by the fact that the meso-metallocenes described give atactic polymers of high molecular weight in the industrially particularly relevant temperature range between $50°$ and $80°$ C. rac/meso mixtures of the metallocenes according to the invention give homogeneous polymers with particular good processing properties. Moldings produced therefrom are distinguished by good surfaces and high transparency. In addition, high surface hardnesses and good moduli of elasticity in flexing are characteristics of these moldings.

The high-molecular-weight atactic component is not tacky, and the moldings are furthermore distinguished by very good fogging behavior.

The examples below serve to illustrate the invention in greater detail.

The following abbreviations are used:

| | |
|---|---|
| VI = | viscosity index in $cm^3/g$ |
| $M_w$ = | weight average molecular weight in g/mol ⎫ determined by |
| $M_w/M_n$ = | polydispersity ⎬ gel permeation chromatography |
| m.p. = | melting point determined by DSC ($20°$ C./min heating/cooling rate) |
| II = | isotactic index (II = mm + ½ mr) determined by $^{13}$C—NMR spectroscopy |
| $n_{iso}$ = | isotactic block length ($n_{iso}$ = 1 + mm/mr) |
| $n_{syn}$ = | syndiotactic block length ($n_{syn}$ = 1 + 2 rr/mr) |

MFI/(230/5)=melt flow index, measured in accordance with DIN 53735; in dg/min.

EXAMPLES 1 TO 16

A dry 24 $dm^3$ reactor was flushed with propylene and filled with 12 $dm^3$ of liquid propylene. 35 $cm^3$ of a toluene solution of methylaluminoxane (corresponding to 52 mmol of Al, mean degree of oligomerization p=18) were then added, and the batch was stirred at 30° C. for 15 minutes. In parallel, 7.5 mg of the meso-metallocene shown in Table 1 were dissolved in 13.5 cm$^3$ of a toluene solution of methylaluminoxane (30 mmol of Al) and preactivated by standing for 15 minutes. The solution was then introduced into the reactor and heated to 70° C. or 50° C. (Table 1, 10° C./min). The polymerization duration was 1 hour. The polymerization was terminated by addition of 20 dm$^3$ (s.t.p.) of $CO_2$ gas. The metallocene activities and the viscosity indices of the atactic polymers obtained are collated in Table 1. The $^{13}$C-NMR analyses gave in all cases isotactic block lengths $n_{iso}$ of <4, typically $h_{iso}$=2, and the syndiotactic block length was typically likewise in the region of 2. The triad distributions mm:mr:rr were typically about 25:50:25, and the isotactic index (mm+½ mr) was less than 60%. The products were therefore undoubtedly typical atactic polypropylenes. This is also confirmed by the solubility in boiling heptane or in diethyl ether.

The DSC spectrum showed no defined melting point. $T_g$ transitions were observed in the range from 0° C. to −20° C.

The polymers obtained were extracted with boiling ether or dissolved in a hydrocarbon having a boiling range of 140°–170° C. and subjected to fractional crystallization; the high-molecular-weight atactic component was separated off and could thus be analyzed separately from the isotactic residue. The results are collated in Table 2. Products are non-tacky, and moldings produced therefrom do not exhibit fogging and have an excellent surface and transparency.

TABLE 1

| Meso-metallocene | Polymerization temperature [°C.] | Activity [kg of PP/g of metallocene × h] | VI [cm$^3$/g] | Ex. |
|---|---|---|---|---|
| Me$_2$Si(2,4-dimethyl-1-indenyl)$_2$ZrCl$_2$ | 50 | 35.7 | 125 | 1 |
| Me$_2$Si(2-methyl-4-isopropyl-1-indenyl)$_2$ZrCl$_2$ | 70 | 60.4 | 93 | 2 |
| Me$_2$Si(2-ethyl-4-methyl-1-indenyl)$_2$ZrCl$_2$ | 70 | 70.3 | 101 | 3 |
| Ph(Me)Si(2-methyl-4-isopropyl-1-indenyl)$_2$ZrCl$_2$ | 50 | 20.6 | 120 | 4 |
| Me$_2$Si(2-methyl-4,5-benzoindenyl)$_2$ZrCl$_2$ | 70 | 200.0 | 120 | 5 |
| Me$_2$Si(2-methyl-4,5-benzoindenyl)$_2$ZrCl$_2$ | 50 | 60.4 | 150 | 6 |
| Me$_2$Si(2,4,6-trimethyl-1-indenyl)$_2$ZrCl$_2$ | 50 | 30.1 | 163 | 7 |
| Me$_2$Si(2-methyl-4,6-diisopropyl-1-indenyl)$_2$ZrCl$_2$ | 50 | 24.5 | 89 | 8 |
| Me$_2$Si(2-methyl-α-acenaphthindenyl)$_2$ZrCl$_2$ | 50 | 49.3 | 224 | 9 |
| Me$_2$Si(2-methyl-α-acenaphthindenyl)$_2$ZrCl$_2$ | 70 | 189.4 | 140 | 10 |
| Me$_2$Si(2-methyl-4-phenylindenyl)$_2$ZrCl$_2$ | 70 | 64.5 | 131 | 11 |
| Me$_2$Si(2-methyl-4-phenyl-1-indenyl)$_2$ZrCl$_2$ | 50 | 32.5 | 169 | 12 |
| Ethylene(2,4,6-trimethyl-1-indenyl)$_2$ZrCl$_2$ | 70 | 145.5 | 124 | 13 |
| Ethylene(2-methyl-4,5-benzoindenyl)$_2$ZrCl$_2$ | 50 | 94.9 | 109 | 14 |
| Methylethylene(2-methyl-α-acenaphthindenyl)$_2$ZrCl$_2$ | 50 | 64.3 | 204 | 15 |
| Ph(Me)Si(2-methyl-α-acenaphthindenyl)$_2$ZrCl$_2$ | 50 | 69.8 | 198 | 16 |

EXAMPLES 17 TO 23

Examples 1, 4, 7, 9, 12, 15 and 16 were repeated but the pure meso-metallocene was replaced by a rac:meso=1:1 mixture.

TABLE 2

| Rac:meso = 1:1 | Activity [kg of PP/g of | Ether-soluble atactic component | | Ether-insoluble isotactic component | |
|---|---|---|---|---|---|
| Ex. metallocene mixture | metallocene × h] | % by weight | VI [cm$^3$/g] | % by weight | VI [cm$^3$/g] |
| 17 Me$_2$Si(2,4-dimethyl-1-indenyl)$_2$ZrCl$_2$ | 69.5 | 25.4 | 117 | 74.6 | 216 |
| 18 Ph(Me)Si(2-methyl-4-isopropyl-1-indenyl)$_2$ZrCl$_2$ | 102.3 | 12.0 | 124 | 88.0 | 280 |
| 19 Me$_2$Si(2,4,6-trimethyl-1-indenyl)$_2$ZrCl$_2$ | 114.0 | 18.5 | 152 | 71.5 | 245 |
| 20 Me$_2$Si(2-methyl-α-acenaphth-indenyl)$_2$ZrCl$_2$ | 61.4 | 44.9 | 209 | 53.1 | 438 |
| 21 Me$_2$Si(Si(2-methyl-4-phenyl-1-indenyl)$_2$ZrCl$_2$ (5 mg) | 334.5 | 5.5 | 177 | 94.5 | 887 |

TABLE 2-continued

| Rac:meso = 1:1 | Activity [kg of PP/g of | Ether-soluble atactic component | | Ether-insoluble isotactic component | |
|---|---|---|---|---|---|
| Ex. metallocene mixture | metallocene × h] | % by weight | VI [cm³/g] | % by weight | VI [cm³/g] |
| 22 Methylethylene(2-methyl-α-acenaphthindenyl)$_2$ZrCl$_2$ | 85.2 | 36.9 | 199 | 63.1 | 365 |
| 23 Ph(Me)Si(2-methyl-α-acenaphthindenyl)$_2$ZrCl$_2$ | 79.1 | 31.2 | 205 | 68.8 | 465 |

EXAMPLES 24 TO 28

Example 5 was repeated, but the pure meso-form of the metallocene was replaced by rac:meso ratios of 98:2, 95:5, 90:10, 85:15 and 75:25. The results are collated in Table 3. A non-tacky powder is obtained, and moldings produced therefrom have a good surface, are non-tacky and do not exhibit fogging. The molding hardness is good, as is the transparency.

TABLE 3

| Ex. | Rac: meso | Activity [kg PP/g metallocene × h] | Ether-soluble atatic component | | Ether-insoluble isotactic component | |
|---|---|---|---|---|---|---|
| | | | % by wt. | VI [cm³/g] | % by wt. | VI [cm³/g] |
| 24 | 98:2 | 436 | 0.95 | 134 | 99.05 | 285 |
| 25 | 95:5 | 410 | 2.7 | 119 | 97.3 | 276 |
| 26 | 90:10 | 415 | 4.3 | 122 | 95.7 | 296 |
| 27 | 85:15 | 370 | 7.3 | 125 | 92.7 | 300 |
| 28 | 75:25 | 347 | 15.2 | 130 | 84.8 | 280 |

EXAMPLE 29

Example 24 was repeated using 12 dm³ (s.t.p.) of hydrogen in the polymerization system. The polymerization duration was 30 minutes. The metallocene activity was 586 kg of PP/g of metallocene×h. The ether-soluble proportion was 1.1% by weight, with a VI of 107 cm³/g, and the ether-insoluble proportion was 98.9% by weight, with a VI of 151 cm³/g.

EXAMPLE 30

Example 25 was repeated, but 70 g of ethylene were metered in continuously during the polymerization. The polymerization duration was 45 minutes. The metallocene activity was 468 kg of PP/g of metallocene×h, the ethylene content of the copolymer was 3.3% by weight, and, according to $^{13}$C-NMR spectroscopy, the ethylene was incorporated substantially in an isolated manner (random coompolymer).

EXAMPLE 31

A dry 150 dm³ reactor was flushed with nitrogen and filled at 20° C. with 80 dm³ of a benzine cut having the boiling range from 100° to 120° C. from which the aromatic components had been removed. The gas space was then flushed with propylene until free of nitrogen, and 50 l of liquid propylene and 64 cm³ of a toluene solution of methylaluminoxane (100 mmol of Al, p=18) were added. The reactor contents were heated to 60° C., and the hydrogen content in the reactor gas space was adjusted to 0.1% by metering in hydrogen and was kept constant during the entire polymerization time by further metering (checking on-line by gas chromatography). 10.7 mg of rac:meso (95:5) of the metallocene dimethylsilanediylbis(2-methyl-4,5-benzoindenyl)zirconium dichloride were dissolved in 32 cm³ of a toluene solution of methylaluminoxane (50 mmol) and introduced into the reactor. The polymerization was carried out in first step for 8 hours at 60° C. In a second step, 2.8 kg of ethylene were added rapidly at 47° C. and, after polymerization for a further 5 hours at this temperature, the polymerization was completed by discharging the reactor contents into a 280 l reactor containing 100 l of acetone. The polymer powder was separated off and dried for 48 hours at 80° C./200 mbar. 21.4 kg of block copolymer powder were obtained. VI=359 cm³/g; M$_w$=402,000 g/mol, M$_w$/M$_n$=4.0; MFI (230/5)=9.3 dg/min. The block copolymer contained 12.2% by weight of ethylene. Fractionation gave a content of 31.5% by weight of ethylene/propylene rubber and 3.7% by weight of atactic polypropylene, with a VI of 117 cm³/g in the polymer as a whole.

EXAMPLE 32

The procedure was as in Examples 1–16, but the metallocene was the compound meso-Me$_2$Si(2-methyl-4-(1-naphthyl)-1-indenyl)$_2$ZrCl$_2$. The results are collated in Table 4.

TABLE 4

| Polymerization temperature [°C.] | Activity [kg of PP/g of metallocene × h] | VI [cm³/g] | M$_w$/M$_n$ | M$_w$ [g/mol] |
|---|---|---|---|---|
| 70 | 58.3 | 205 | 2.0 | 249 500 |
| 50 | 31.7 | 335 | 2.1 | 425 500 |

EXAMPLE 33

The procedure was as in Example 32, but the metallocene was Ph(Me)Si(2-methyl-4-phenyl-1-indenyl)$_2$ZrCl$_2$ and was employed as a 1:1 meso:rac mixture. The results are collated in Table 5.

TABLE 5

| Polymerization temperature [°C.] | Activity [kg of PP/g of metallocene × h] | VI [cm³/g] | M$_w$/M$_n$ | M$_w$ [g/mol] |
|---|---|---|---|---|
| 70 | 112.5 | 559 | 3.5 | 738 000 |
| 50 | 51.0 | 1084 | 3.6 | 1.35 · 10$^6$ |

Fractionation of the polymer samples by ether extraction gave contents of atactic polypropylene of 3.6% by weight (polymerization temperature of 50° C.) and 7.0% by weight (polymerization temperature of 70° C.). The VI values were 158 and 106 cm³/g respectively.

The isolated atactic component had an elastomeric consistency and was completely transparent.

The polymer powder obtained from the polymerization is non-tacky, and moldings produced therefrom have a good surface, are very transparent and do not exhibit fogging.

EXAMPLE 34

The process was as in Example 32, but the metallocene used was rac/meso-Me$_2$Si(2-methyl-4-phenyl-1-indenyl)$_2$ZrCl$_2$ in supported form, with a rac:meso ratio of 1:1. The supported metallocene was prepared in the following way:

a) Preparation of the supported cocatalyst

The supported cocatalyst was prepared as described in EP 92 107 331.8 in the following way in an explosion-proofed stainless-steel reactor fitted with a 60 bar pump system, inert-gas supply, temperature control by jacket cooling and a second cooling circuit via a heat exchanger in the pump system. The pump system drew the contents out of the reactor via a connector in the reactor base into a mixer and back into the reactor through a riser pipe via a heat exchanger. The mixer was installed in such a way that a narrowed tube cross-section, where an increased flow rate occurred, was formed in the feed line, and a thin feed line through which—in cycles—in each case a defined amount of water under 40 bar of argon could be fed in ran into its turbulence zone axially and against the flow direction. The reaction was monitored via a sampler in the pump circuit.

5 dm$^3$ of decane were introduced under inert conditions into the above-described reactor with a capacity of 16 dm$^3$. 0.3 dm$^3$ (=3.1 mol) of trimethylaluminum were added at 25° C. 250 g of silica gel SD 3216-30 (Grace AG) which had previously been dried at 120° C. in an argon fluidized bed were then metered into the reactor via a solids funnel and homogeneously distributed with the aid of the stirrer and the pump system. The total amount of 45.9 g of water was added to the reactor in portions of 0.1 cm$^3$ every 15 seconds over the course of 2 hours. The pressure, caused by the argon and the evolved gases, was kept constant at 10 bar by pressure-regulation valves. When all the water had been introduced, the pump system was switched off and the stirring was continued at 25° C. for a further 5 hours. The solvent was removed via a pressure filter, and the cocatalyst solid was washed with decane and then dried in vacuo. The isolated solid contains 19.5% by weight of aluminum. 15 g of this solid (108 mmol of Al) were suspended in 100 cm$^3$ of toluene in a stirrable vessel and cooled to −30° C. At the same time, 200 mg (0.317 mmol) of rac/meso 1:1 Me$_2$Si(2-methyl-4-phenyl-indenyl)$_2$ZrCl$_2$ were dissolved in 75 cm$^3$ of toluene and added dropwise to the suspension over the course of 30 minutes. The mixture was slowly warmed to room temperature with stirring, during which time the suspension took on a red color. The mixture was subsequently stirred at 70° C. for 1 hour, cooled to room temperature and filtered, and the solid was washed 3 times with 100 cm$^3$ of toluene in each case and once with 100 cm$^3$ of hexane. The hexane-moist filter residue which remained was dried in vacuo, giving 14.1 g of free-flowing, pink supported catalyst. Analysis gave a content of 11.9 mg of zirconocene per gram of catalyst.

b) Polymerization 0.7 g of the catalyst prepared under a) were suspended in 50 cm$^3$ of a benzine fraction having the boiling range 100°–120° C. from which the aromatic components had been removed.

In parallel, a dry 24 dm$^3$ reactor was flushed first with nitrogen and subsequently with propylene and filled with 12 dm$^3$ of liquid propylene and with 1.5 dm$^3$ of hydrogen. 3 cm$^3$ of triisobutylaluminum (12 mmol) were then diluted with 30 ml of hexane and introduced into the reactor, and the batch was stirred at 30° C. for 15 minutes. The catalyst suspension was subsequently introduced into the reactor, and the polymerization system was heated to the polymerization temperature of 70° C. (10° C./min) and kept at 70° C. for 1 hour by cooling. The polymerization was terminated by addition of 20 mol of isopropanol. The excess monomer was removed as a gas, and the polymer was dried in vacuo, giving 1.57 kg of polypropylene powder.

Fractionation of the polymer by ether extraction gave an ether-soluble atactic content of 8.9% by weight (VI= 149 cm$^3$/g) and an insoluble isotactic content of 91.1% by weight, with a VI of 489 cm$^3$/g. The powder prepared in this way was non-tacky, and moldings produced therefrom do not exhibit fogging in the heat-aging test, and the hardness and transparency of the moldings are very good.

COMPARATIVE EXAMPLES 1 TO 10

Polymerization were carried out in a manner comparable to the above examples using 1:1 rac:meso mixtures of metallocenes not according to the invention at polymerization temperatures of 70° C. and 30° C. The resultant polymers were likewise subjected to ether separation in order to characterize the polymer components. The results are collated in Table 6 and show that in no case could a polymer according to the invention having a high-molecular-weight atactic polymer component (ether-soluble component) be prepared. Products are generally tacky, and the moldings produced therefrom are soft, have a speckled surface and exhibit considerable fogging.

TABLE 6

| Metallocene rac:meso = 1:1 mixture | Polymerization temperature 70° C. | | Polymerization temperature 30° C. | |
|---|---|---|---|---|
| | VI ether-soluble [cm$^3$/g] | VI ether-soluble [cm$^3$/g] | VI ether-soluble [cm$^3$/g] | VI ether-soluble [cm$^3$/g] |
| Me$_2$Si(indenyl)$_2$ZrCl$_2$ | 45 | 42 | 46 | 75 |
| Me$_2$Si(2-methyl-1-indenyl)$_2$ZrCl$_2$ | 50 | 180 | 56 | 340 |
| Methylethylene(2-methyl-1-indenyl)$_2$ZrCl$_2$ | 56 | 127 | 59 | 409 |
| Ph(Me)Si(2-methyl-1-indenyl)$_2$ZrCl$_2$ | 50 | 202 | 57 | 501 |

TABLE 6-continued

| | Polymer data | | | |
|---|---|---|---|---|
| | Polymerization temperature 70° C. | | Polymerization temperature 30° C. | |
| Metallocene rac:meso = 1:1 mixture | VI ether-soluble [cm³/g] | VI ether-soluble [cm³/g] | VI ether-soluble [cm³/g] | VI ether-soluble [cm³/g] |
| Me₂Si(2-ethyl-1-indenyl)₂ZrCl₂ | 59 | 187 | 61 | 443 |
| Me₂Si(2,4,5-trimethyl-1-cyclopentadienyl)₂ZrCl₂ | 45 | 50 | 47 | 236 |
| Me₂Si(2,4,5-trimethyl-1-cyclopentadienyl)₂HfCl₂ | 59 | 175 | 69 | 356 |
| Me₂Si(indenyl)₂HfCl₂ | 61 | 237 | 63 | 398 |
| Ethylene(2-methyl-1-indenyl)₂ZrCl₂ | 47 | 85 | 50 | 135 |
| Me₂Si(2-methyl-4-t-butyl-1-cyclopentadienyl)₂ZrCl₂ | 28 | 31 | 35 | 105 |

COMPARATIVE EXAMPLES 11 TO 21

Comparative Examples 1 to 10 were repeated using the pure meso-forms of the metallocenes used therein. Atactic polypropylene was obtained, but in no case was a viscosity index VI of >70 cm³/g obtained. These metallocenes which are not according to the invention can thus not be used to prepare high-molecular-weight atactic polypropylene. The products are liquid or at least soft and highly tacky.

What is claimed is:

1. A process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from −60° to 200° C., at a pressure of from 0.5 to 100 bar, in solution, in suspension or in the gas phase, in the presence of a catalyst formed from a metallocene in the meso-form or a meso:rac mixture, with meso:rac >1:99, as transition-metal compound and a cocatalyst, wherein the metallocene is a compound of the formula I,

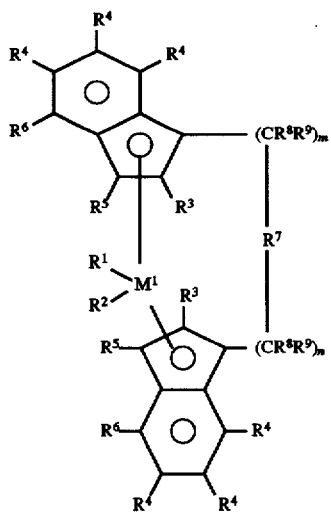

in which $M^1$ is a metal from group IVb, Vb or VIb of the Periodic Table, $R^1$ and $R^2$ are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group, or a halogen atom, the radicals $R^4$ and $R^5$ are identical or different and are a hydrogen atom, a halogen atom, a $C_1$-$C_{10}$-alkyl group, which may be halogenated, a $C_6$-$C_{10}$-aryl group, which may be halogenated, and an —NR$^{10}$₂, —SR$^{10}$, —OSiR$^{10}$₃, —SiR$^{10}$₃ or —PR$^{10}$₂ radical in which $R^{10}$ is a halogen atom, a $C_1$-$C_{10}$-alkyl group or a $C_6$-$C_{10}$-aryl group, $R^3$ and $R^6$ are identical or different and are as defined as for $R^4$, with the proviso that $R^3$ and $R^6$ are not hydrogen, or two or more of the radicals $R^3$ to $R^6$, together with the atoms connecting them, form a ring system, $R^7$ is $$-\underset{R^{12}}{\overset{R^{11}}{M^2}}-, \quad -\underset{R^{12}}{\overset{R^{11}}{M^2}}-\underset{R^{12}}{\overset{R^{11}}{M^2}}-, \quad -\underset{R^{12}}{\overset{R^{11}}{M^2}}-(CR_2^{13})-, \quad -O-\underset{R^{12}}{\overset{R^{11}}{M^2}}-O-$$

$$-\underset{R^{12}}{\overset{R^{11}}{C}}-, \quad -O-\underset{R^{12}}{\overset{R^{11}}{M^2}}-,$$

>BR$^{11}$, >AlR$^{11}$, —Ge—, —Sn—, —O—, —S—, >SO, >SO₂, >NR$^{11}$, >CO, >PR$^{11}$ or >P(O)R$^{11}$, where $R^{11}$, $R^{12}$ and $R^{13}$ are identical or different and are a hydrogen atom, a halogen atom, a $C_1$-$C_{10}$-alkyl group, a $C_1$-$C_{10}$-fluoroalkyl group, a $C_6$-$C_{10}$-aryl group, a $C_6$-$C_{10}$-fluoroaryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or $R^{11}$ and $R^{12}$ or $R^{11}$ and $R^{13}$, in each case together with the atoms connecting them, form a ring, $M^2$ is silicon, germanium or tin, $R^8$ and $R^9$ are identical or different and are as defined for $R^{11}$, and m and n are identical or different and are zero, 1 or 2, where m plus n is zero, 1 or 2.

2. The process as claimed in claim 1, wherein, in the formula I, $M^1$ is Zr or Hf, $R^1$ and $R^2$ are identical or different and are methyl or chlorine, $R^3$ and $R^6$ are identical or different and are methyl, isopropyl, phenyl, ethyl or trifluoromethyl, $R^4$ and $R^5$ are hydrogen or as defined for $R^3$ and $R^6$, or $R^4$ forms an aliphatic or aromatic ring with $R^6$, or adjacent radicals $R^4$ form a ring of this type, and $R^7$ is a

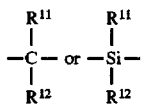

radical, and m plus n are zero or 1.

3. The process as claimed in claim 1, wherein the metallocene of the formula I is the rac:meso>1:99 form or the pure meso-form of the compounds Me$_2$Si(2,4-dimethyl-1-indenyl)$_2$ZrCl$_2$ Me$_2$Si(2-methyl-4-isopropyl-1-indenyl)$_2$ZrCl$_2$, Me$_2$Si(2-ethyl-4 -methyl-1-indenyl)$_2$ZrCl$_2$, Ph(Me)Si(2-methyl-4-isopropyl-1-indenyl)$_2$ZrCl$_2$, Me$_2$Si(2-methyl-4,5-benzoindenyl)$_2$ZrCl$_2$, Me$_2$Si(2,4,6-trimethyl-1-indenyl)$_2$ZrCl$_2$, Me$_2$Si(2-methyl-4,6-diisopropyl-1-indenyl)$_2$ZrCl$_2$, Me$_2$Si(2-methyl-α-acenaphthindenyl)$_2$ZrCl$_2$, Me$_2$Si(2-methyl-4-phenyl-1-indenyl)$_2$ZrCl$_2$, ethylene(2,4,6-trimethyl-1-indenyl)$_2$ZrCl$_2$, ethylene(2-methyl-4,5-benzoindenyl)$_2$ZrCl$_2$, methylethylene(2-methyl-α-acenaphthindenyl) $_2$ZrCl$_2$, Me$_2$Si(2-methyl-4-(1-naphthyl)-1-indenyl)$_2$ZrCl$_2$, Ph(Me)Si(2-methyl-4-phenyl-1-indenyl)$_2$ZrCl$_2$ or Ph(Me)Si(2-methyl-α-acenaphthindenyl)$_2$ZrCl$_2$.

4. The process as claimed in claim 1, wherein the cocatalyst used is an aluminoxane of the formula (II)

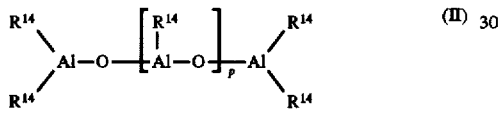

for the linear type and/or of the formula (III)

for the cyclic type, where, in the formulae (II) and (III), the radicals $R^{14}$ are identical or different and are a $C_1$-$C_6$-alkyl group, a $C_6$-$C_{18}$-aryl group, benzyl or hydrogen, and p is an integer from 2 to 50.

5. The process as claimed in claim 1, wherein the cocatalyst used is methylaluminoxane.

6. The process as claimed in claim 4, wherein the metallocene of the formula I is preactivated by means of an aluminoxane of the formula II and/or III before use in the polymerization reaction.

7. The process as claimed in claim 1, wherein the meso-form of the metallocene of the formula I is used to prepare a polyolefin having a viscosity index VI of >80 cm$^3$/g, a molecular weight $M_w$ of >100,000 g/mol, a polydispersity $M_w/M_n$ of ≦4.0 and an isotactic index of ≦60%.

8. The process as claimed in claim 1, wherein a meso:rac>1:99 mixture of the metallocene of the formula I is used to prepare a polyolefin which comprises at least two types of polyolefin chains:

a) a maximum of 99% by weight of the polymer chains comprise isotactically linked α-olefin units having an isotactic index of >90% and a polydispersity of ≦4.0, and b) at least 1% by weight of polymer chains comprise atactic polyolefins having an isotactic index of ≦60%, a viscosity index VI of >80 cm$^3$/g, a molecular weight $M_w$ of >100,000 g/mol and a polydispersity $M_w/M_n$ of ≦4.0.

9. A process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from –60° to 200° C., at a pressure of 0.5 to 100 bar, in solution, in suspension or in the gas phase, in the presence of a catalyst formed from a metallocene in the meso-form or a meso:rac mixture, with meso:rac>1:99, as transition-metal compound and a cocatalyst, wherein the metallocene is a compound of the formula I,

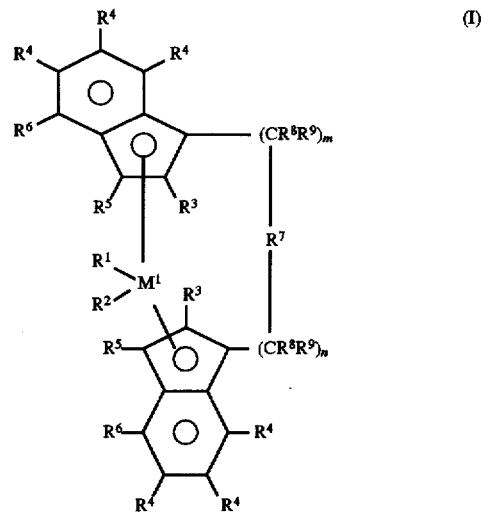

in which $M^1$ is a metal from group IVb, Vb or VIb of the Periodic Table, $R^1$ and $R^2$ are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group, or a halogen atom, the radicals $R^4$, $R^{'4}$ and $R^5$ are identical or different and are a halogen atom, a $C_1$-$C_{10}$-alkyl group, which may be halogenated, a $C_6$-$C_{10}$-aryl group, which may be halogenated, and an —NR$^{10}{}_2$, —SR$^{10}$, —OSiR$^{10}{}_3$, —SIR$^{10}{}_3$ or —PR$^{10}{}_2$ radical in which $R^{10}$ is a halogen atom, a $C_1$-$C_{10}$-alkyl group or a $C_6$-$C_{10}$-aryl group, and additionally, $R^4$ and $R^5$ can also be hydrogen, $R^3$ and $R^6$ are identical or different and are as defined for $R^4$, with the proviso that $R^3$ and $R^6$ are not hydrogen, or two or more of the radicals $R^3$ to $R^6$, together with the atoms connecting them, form a ring system, $R^7$ is

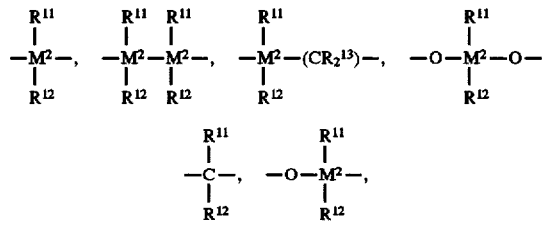

>BR$^{11}$, >AlR$^{11}$, —Ge—, —Sn—, —O—, —, >SO, >SO$_2$, >NR$^{11}$, >CO, >PR$^{11}$ or >P(O)R$^{11}$, where R$^{11}$, $R^{12}$, and $R^{13}$ are identical or different and are a hydrogen atom, a halogen atom, a $C_1$-$C_{10}$-alkyl group, a $C_1$-$C_{10}$-fluoroalkyl group, a $C_6$-$C_{10}$-aryl group, a $C_6$-$C_{10}$-fluoroaryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or $R^{11}$ and $R^{12}$ or $R^{11}$ and $R^{13}$, in each case together with atoms connecting them, form a ring, $M^2$ is silicon, germanium or tin, $R^8$ and $R^9$ are identical or different and are as defined for $R^{11}$, and m and n are identical or different and are zero, 1 or 2, where m plus n is zero, 1 or 2.

10. A method of using a metallocene as a catalyst in the preparation of an olefin polymer by polymerizing or copolymerizing an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from –60° to 200° C., at a pressure of 0.5 to 100 bar, in solution, in suspension or in the gas phase, in the presence of the metallocene catalyst and a cocatalyst, where the metallocene is a compound of the formula I in its pure meso-form or as a meso:rac>1:99 mixture

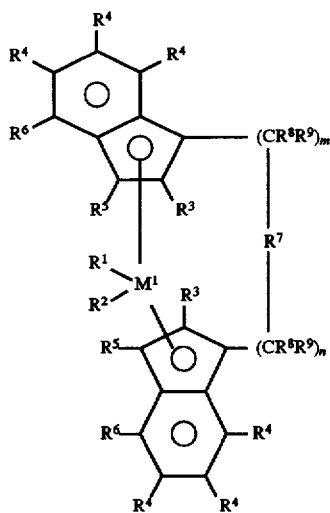

(I)

in which $M^1$ is a metal from group IVb, Vb or VIb of the Periodic Table, $R^1$ and $R^2$ are identical or different and are a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group, a $C_8$-$C_{40}$-arylalkenyl group, or a halogen atom, the radicals $R^4$ and $R^5$ are a hydrogen atom, identical or different and are a halogen atom, a $C_1$-$C_{10}$-alkyl group, which may be halogenated, a $C_6$-$C_{10}$-aryl group, which may be halogenated, and an —$NR^{10}{}_2$, —$SR^{10}$, —$OSiR^{10}{}_3$, —$SiR^{10}{}_3$ or —$PR^{10}{}_2$ radical in which $R^{10}$ is a halogen atom, a $C_1$-$C_{10}$-alkyl group or a $C_6$-$C_{10}$-aryl group, $R^3$ and $R^6$ are identical or different and are as defined for $R^4$, with the proviso that $R^3$ and $R^6$ are not hydrogen, or two or more of the radicals $R^3$ to $R^6$, together with the atoms connecting them, form a ring system, $R^7$ is

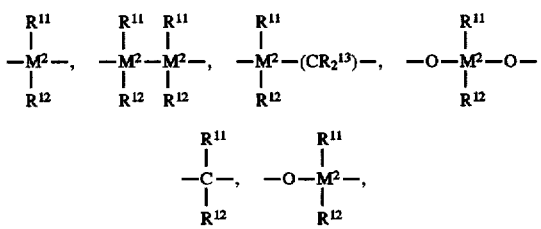

>$BR^{11}$, >$AlR^{11}$, —Ge—, —Sn—, —O—, —S—, >SO, >$SO_2$, >$NR^{11}$, >CO, >$PR^{11}$ or >$P(O)R^{11}$, where $R^{11}$, $R^{12}$, and $R^{13}$ are identical or different and are a hydrogen atom, a halogen atom, a $C_1$-$C_{10}$-alkyl group, a $C_1$-$C_{10}$-fluoroalkyl group, a $C_6$-$C_{10}$-aryl group, a $C_6$-$C_{10}$-fluoroaryl group, a $C_1$-$C_{10}$-alkoxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group, or $R^{11}$ and $R^{12}$ or $R^{11}$ and $R^{13}$, in each case together with atoms connecting them, form a ring, $M^2$ is silicon, germanium or tin, $R^8$ and $R^9$ are identical or different and are as defined for $R^{11}$, and m and n are identical or different and are zero, 1 or 2, where m plus n is zero, 1 or 2.

* * * * *

UNITED STATES PATENT AND TRADEMARK OFFICE
CERTIFICATE OF CORRECTION

PATENT NO.    : 5,672,668  Page 1 of 1
DATED         : September 30, 1997
INVENTOR(S)   : Winter et al.

It is certified that error appears in the above-identified patent and that said Letters Patent is hereby corrected as shown below:

Title page,
Item [*] Notice, please correct to read:

-- The term of this patent shall not extend beyond the expiration date of U.S. Patent No. 5,278,264 --.

Column 18,
Figure (I) should be:

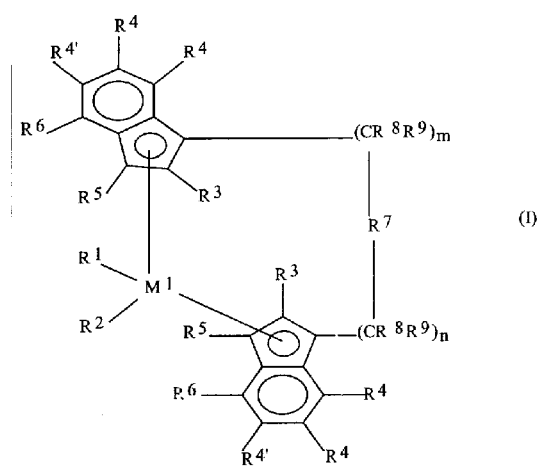

Signed and Sealed this

Twentieth Day of May, 2003

JAMES E. ROGAN
*Director of the United States Patent and Trademark Office*